United States Patent
Boyd et al.

(10) Patent No.: US 11,058,893 B2
(45) Date of Patent: Jul. 13, 2021

(54) KILOVOLTAGE RADIATION THERAPY

(71) Applicant: Precision RT, Inc., Las Vegas, NV (US)

(72) Inventors: Douglas P. Boyd, Las Vegas, NV (US); Michael Weil, Half Moon Bay, CA (US); Samuel M. Song, Las Vegas, NV (US)

(73) Assignee: Precision RT Inc., Las Vegas, NV (US)

( * ) Notice: Subject to any disclaimer, the term of this patent is extended or adjusted under 35 U.S.C. 154(b) by 0 days.

(21) Appl. No.: 15/722,979

(22) Filed: Oct. 2, 2017

(65) Prior Publication Data

US 2018/0345039 A1    Dec. 6, 2018

Related U.S. Application Data

(60) Provisional application No. 62/514,466, filed on Jun. 2, 2017.

(51) Int. Cl.
*A61N 5/10* (2006.01)
*H01J 35/12* (2006.01)
(Continued)

(52) U.S. Cl.
CPC ......... *A61N 5/1043* (2013.01); *A61N 5/1049* (2013.01); *A61N 5/1067* (2013.01);
(Continued)

(58) Field of Classification Search
CPC ...... A61N 5/1045; A61N 5/10; A61N 5/1031; A61N 5/1049; A61N 5/1067; A61N 5/1069; A61N 2005/1074; A61N 2005/1091
(Continued)

(56) References Cited

U.S. PATENT DOCUMENTS

| 5,335,255 A | * | 8/1994 | Seppi | A61B 6/032 378/134 |
| 5,541,975 A | * | 7/1996 | Anderson | H05G 1/025 378/130 |

(Continued)

FOREIGN PATENT DOCUMENTS

| CN | 103889135 A | 6/2014 |
| CN | 104616952 A | 5/2015 |

(Continued)

OTHER PUBLICATIONS

European Patent Office, Extended European Search Report for European Patent Application No. 18170091.5, 6 pages, dated Oct. 24, 2018.

*Primary Examiner* — Thomas R Artman
(74) *Attorney, Agent, or Firm* — Viksnins Harris Padys Malen LLP (57) ABSTRACT

Apparatus and methods to deliver kV X-rays toward a target lesion within a body including: a treatment anode configured to receive electron beams and output the kV X-rays through a specially-designed collimator; an electron beam source configured to generate and direct the electron beams toward the treatment anode; and at least one magnet configured to steer and scan the electron beams along the treatment anode to prevent overheating of the treatment anode. The components are mounted on a gantry that rotates about the target lesion to distribute the dose delivered over a large volume of healthy tissue while substantially maximizing the dose delivered to the target lesion.

20 Claims, 9 Drawing Sheets

(51) Int. Cl.
*H01J 35/14* (2006.01)
*H01J 35/30* (2006.01)
*H01J 35/08* (2006.01)
*H05G 1/70* (2006.01)

(52) U.S. Cl.
CPC ............ *H01J 35/112* (2019.05); *H01J 35/13* (2019.05); *H01J 35/153* (2019.05); *H01J 35/30* (2013.01); *H05G 1/70* (2013.01); *A61N 5/1069* (2013.01); *A61N 2005/1054* (2013.01); *A61N 2005/1061* (2013.01); *A61N 2005/1091* (2013.01)

(58) Field of Classification Search
USPC .......................................................... 378/65
See application file for complete search history.

(56) References Cited

U.S. PATENT DOCUMENTS

| | | | | | |
|---|---|---|---|---|---|
| 5,751,784 | A * | 5/1998 | Enck | ........................ | H01J 35/30 378/119 |
| 5,892,749 | A * | 4/1999 | Yamanaka | ............ | G11B 7/1356 369/112.17 |
| 6,327,340 | B1 * | 12/2001 | Runnoe | ................. | H01J 35/107 378/130 |
| 8,050,384 | B2 * | 11/2011 | Carol | ........................ | A61N 5/10 378/65 |
| 8,306,184 | B2 * | 11/2012 | Chang | ................... | A61N 5/103 378/62 |
| 8,625,738 | B2 * | 1/2014 | Boyd | ................... | A61N 5/1049 378/65 |
| 8,644,452 | B2 * | 2/2014 | Carol | ................... | A61N 5/1031 378/65 |
| 9,409,040 | B2 * | 8/2016 | Carol | ................... | A61N 5/1031 |
| 9,583,302 | B2 * | 2/2017 | Figueroa Saavedra | ...................... | H01J 35/14 |
| 9,931,522 | B2 * | 4/2018 | Bharadwaj | ............. | H05H 9/048 |
| 10,124,194 | B2 * | 11/2018 | Dilmanian | ........... | A61N 5/1084 |
| 10,702,711 | B2 * | 7/2020 | Kundapur | ................ | A61N 5/1045 |
| 10,814,146 | B2 * | 10/2020 | Dilmanian | ................ | A61B 6/06 |
| 10,839,973 | B2 * | 11/2020 | Muehlhauser | ......... | G21K 1/025 |
| 2001/0043666 | A1 * | 11/2001 | Watanabe | ........... | G03F 7/70058 378/34 |
| 2004/0067014 | A1 * | 4/2004 | Hollars | ............. | G02B 6/29365 385/33 |
| 2005/0276377 | A1 * | 12/2005 | Carol | ................... | A61N 5/1037 378/65 |
| 2007/0016014 | A1 * | 1/2007 | Hara | ........................ | A61N 5/10 600/426 |
| 2007/0076851 | A1 * | 4/2007 | Pellegrino | ............... | G21K 1/10 378/157 |
| 2007/0274446 | A1 * | 11/2007 | Schildkraut | ........... | A61N 5/1049 378/65 |
| 2008/0043916 | A1 * | 2/2008 | Lemaitre | .................. | H05G 1/36 378/113 |
| 2008/0049897 | A1 * | 2/2008 | Molloy | ................. | A61N 5/1042 378/65 |
| 2008/0112539 | A1 * | 5/2008 | Frenk | ....................... | H05G 1/04 378/141 |
| 2009/0154646 | A1 * | 6/2009 | Carol | ........................ | A61N 5/10 378/65 |
| 2010/0166144 | A1 * | 7/2010 | Boyd | .................... | A61N 5/1049 378/62 |
| 2010/0260317 | A1 * | 10/2010 | Chang | .................... | A61N 5/103 378/62 |
| 2011/0075810 | A1 * | 3/2011 | Sendai | ..................... | G21K 1/10 378/95 |
| 2011/0085332 | A1 * | 4/2011 | Vissenberg | .......... | G02B 6/0011 362/235 |
| 2012/0093293 | A1 * | 4/2012 | Carol | .................... | A61N 5/1039 378/65 |
| 2012/0189102 | A1 * | 7/2012 | Maurer, Jr. | ............ | A61B 6/035 378/65 |
| 2014/0086380 | A1 * | 3/2014 | Song | ........................ | A61B 6/032 378/4 |
| 2014/0112451 | A1 * | 4/2014 | Figueroa Saavedra | ...................... | A61N 5/1042 378/137 |
| 2014/0169523 | A1 * | 6/2014 | Frontera | ................ | H01J 35/147 378/62 |
| 2014/0205067 | A1 * | 7/2014 | Carol | .................... | A61N 5/1031 378/65 |
| 2014/0247923 | A1 * | 9/2014 | Park | ........................ | H01J 35/14 378/138 |
| 2015/0055751 | A1 * | 2/2015 | Funk | .................... | A61B 6/4035 378/62 |
| 2015/0065777 | A1 * | 3/2015 | Darwish | ............... | A61N 5/1081 600/1 |
| 2015/0230766 | A1 * | 8/2015 | Wang | ..................... | A61B 6/037 600/411 |
| 2016/0106387 | A1 * | 4/2016 | Kahn | ..................... | A61B 6/5211 378/62 |
| 2016/0166225 | A1 * | 6/2016 | Funk | ..................... | A61B 6/4035 378/146 |
| 2016/0203885 | A1 * | 7/2016 | Song | ................... | H01L 23/3733 378/16 |
| 2016/0225572 | A1 * | 8/2016 | Yanagisawa | ............ | H01J 35/08 |
| 2016/0303400 | A1 * | 10/2016 | Maurer, Jr. | ........... | A61N 5/1049 |
| 2017/0036043 | A1 * | 2/2017 | Dilmanian | ................ | A61B 6/06 |
| 2017/0042489 | A1 * | 2/2017 | Boyd | ..................... | A61B 6/025 |
| 2017/0148606 | A1 * | 5/2017 | Hirayama | ............. | H01J 35/305 |
| 2017/0318651 | A1 * | 11/2017 | Canfield | ............... | H05G 1/52 |
| 2018/0068823 | A1 * | 3/2018 | Utschig | ................ | H01J 35/153 |
| 2018/0330910 | A1 * | 11/2018 | Seki | ..................... | H01J 35/101 |
| 2018/0345039 | A1 * | 12/2018 | Boyd | ....................... | A61N 5/10 |
| 2019/0022423 | A1 * | 1/2019 | Dilmanian | ............ | A61N 5/1084 |
| 2020/0038685 | A1 * | 2/2020 | Kundapur | ............ | A61N 5/1045 |

FOREIGN PATENT DOCUMENTS

| | | |
|---|---|---|
| CN | 104882350 A | 9/2015 |
| WO | 2004037088 A1 | 5/2004 |
| WO | 2015066246 A1 | 5/2015 |

\* cited by examiner

KILOVOLTAGE RADIATION THERAPY

CROSS-REFERENCE TO RELATED APPLICATIONS

This application claims the benefit of priority under 35 U.S.C. § 119(e) of U.S. Provisional Patent Application No. 62/514,466, filed Jun. 2, 2017, entitled "System for Kilovoltage Radiation Therapy." The disclosure of the above-referenced application is incorporated herein by reference.

BACKGROUND

Field of the Disclosure

The present disclosure relates to delivering X-ray radiation to a target lesion, and more specifically, to delivering the X-ray radiation using a treatment anode and a plurality of imaging anodes.

Background

Struggling economies have little chance of surmounting major infrastructure gaps and lack of skilled professionals for medical delivery. Despite the exponential growth in medical technology and data analysis, directed and cost-effective therapies have been lacking for many of the most common lethal diseases. In this context, cancer continues to be a major burden and challenge for worldwide healthcare delivery. Although standard radiation therapy systems for cancer can be effective in treating most cancers, the radiation therapy systems are expensive and complex. Thus, the use of the radiation therapy systems is severely limited in the developing countries, and even in the developed countries, the distribution of the radiation therapy systems is often uneven. Accordingly, reducing the capital equipment cost for the radiation therapy can be important.

SUMMARY

The present disclosure is directed to delivering X-ray radiation. In one implementation, the X-ray radiation is delivered to a target lesion using a treatment anode and a plurality of imaging anodes. Components are mounted on a gantry that rotates about the target lesion to distribute the dose delivered over a large volume of healthy tissue while substantially maximizing the dose delivered to the target lesion.

In one implementation, an apparatus for delivering kV X-rays toward a target lesion within a body is disclosed. The apparatus includes: a treatment anode configured to receive electron beams and output the kV X-rays; an electron beam source configured to generate and direct the electron beams toward the treatment anode; and one or more magnets configured to steer and scan the electron beams along the treatment anode that is water-cooled to prevent overheating of the treatment anode.

In another implementation, a method for delivering kilo-voltage (kV) X-rays toward a target lesion within a body is disclosed. The method includes: generating and directing electron beams toward a treatment anode; steering and scanning the electron beams along the treatment anode using one or more magnets so that the treatment anode generates the kV X-rays; blocking out all of the kV X-rays not directed to a convergence point centered at the target lesion using a specially-designed collimator; and rotating the source of electron beams, the one or more magnets, the treatment anode, and the collimator around the target lesion.

Other features and advantages should be apparent from the present description which illustrates, by way of example, aspects of the disclosure.

BRIEF DESCRIPTION OF THE DRAWINGS

The details of the present disclosure, both as to its structure and operation, may be gleaned in part by study of the appended drawings, in which like reference numerals refer to like parts, and in which.

DETAILED DESCRIPTION

In the past, the medical use of kilo-voltage (kV) X-rays has been limited to superficial radiation therapy due to the high attenuation of the kV X-rays through healthy tissue upstream from the target lesion, especially the superficial skin. In particular, the conventional use of the kV X-rays is currently only available for superficial treatments due to: (1) the difficulty in distributing dose over a large area with a single focal spot; and (2) the fact that most X-ray tubes and power supplies are for imaging purposes (~120 kVp) and cannot run at high power for long periods of time due to over-heating. Although the MV systems are usually used for treating deep lesions, the cost of using the MV systems may be very high. The MV systems are also bulky and may require a large volume of space to house the systems. Further, the high energy radiation of the target lesion from the MV systems may cause much damage to the surrounding healthy tissues.

To address the above-described issues with the conventional radiation systems and uses, several implementations of the present disclosure are directed to a kV radiation therapy system that employs the scanning electron beam technology with collimators and detectors designed for combined therapy and imaging. The kV radiation therapy system of the present disclosure is configured to overcome both of the above-stated issues with the conventional radiation systems using a scanning electron beam X-ray tube that is mounted on a gantry and water-cooled anodes to keep the tungsten anodes from damage.

Experiments have shown that with a 130 kV, 600 mA source with 1×8 mm$^2$ focal spot, tungsten starts to blister at 0.7 msec and melt at 1.0 msec of exposure. Since dwelling the electron beam on tungsten anode can easily destroy the anode, in one implementation, the tungsten anode is kept cool and the electron beam is kept moving ("scanning") at all time using one or more magnets. Further, the electron beam is defocused to increase the focal spot size and thus keep the tungsten from melting. Accordingly, the kV radiation therapy system of the present disclosure is configured to (1) water-cool the anode (tungsten on copper block), (2) defocus the electron beam (e.g., to 1 cm$^2$), and (3) constantly move the beam.

In one implementation, the kV radiation therapy system of the present disclosure includes an intensity-modulated kV X-ray source with a 3-D trajectory, which is achieved by adapting rotation therapy with a gantry and the magnetically-steered continuously scanning electron beam. Thus, the electron beam is swept electronically along the long axis of the treatment anode and moves substantially perpendicularly to that by mechanical motion. The result is an inverted pyramid shape of photons with the apex on the target lesion. This is in contrast to the conventional X-ray sources having electron beams that dwell over a predetermined number of collimators. For the present system, the scan speed and the beam current over the anode can be adjusted to modulate the dose rate in real-time, as the electron beam is steered by the steering magnets. Moreover, moving the electron beam slower delivers more dose (at the current beam position).

The implementations of the present disclosure provide advantages over the conventional systems at relatively low cost with minimal updates to existing infrastructure. Since the cost of kV components and shielding requirements (e.g., multimillion-dollar underground bunkers with two-meter thick concrete walls typically used for MV radiation shielding) are lower than the cost of the conventional components and requirements, the overall cost of the kV radiation therapy system is lower. The cost of the kV radiation therapy system of the present disclosure is estimated to be less than 20% of the cost of conventional MV linac systems. The shielding for 200 kVp X-rays will only require 3 mm of lead in the walls so that ordinary rooms can easily be shielded.

After reading these descriptions, it will become apparent how to implement the disclosure in various implementations and applications. However, although various implementations of the present disclosure will be described herein, it is understood that these implementations are presented by way of example only, and not limitation. As such, this detailed description of various implementations should not be construed to limit the scope or breadth of the present disclosure.

In one implementation, the kV radiation therapy system of the present disclosure provides combined therapy and imaging to enable real-time tracking of lesions for delivering therapy beam precisely to the target lesion. The dosimetry (which is the measurement, calculation, and assessment of the ionizing radiation dose absorbed by the human body) of the proposed energy range (180-300 kV at 130-220 mA, respectively) has been found to be comparable to the MV beams often used in conventional radiation therapy systems.

Figure 1A:
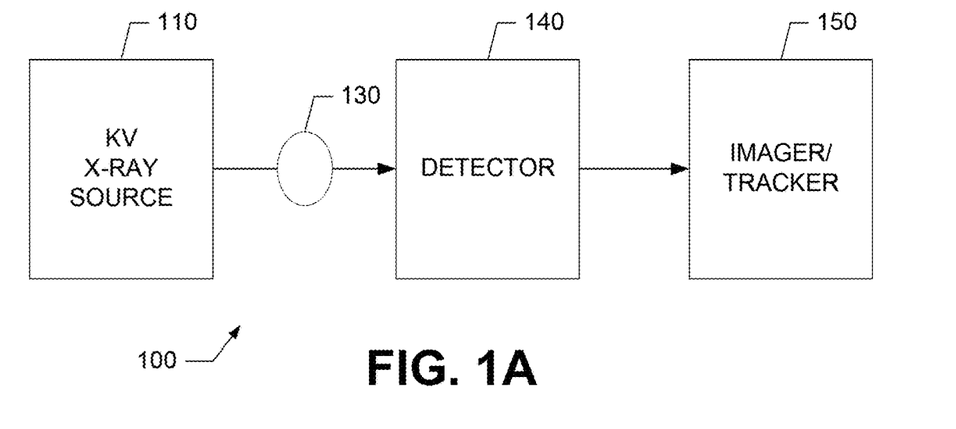
FIG. 1A is a block diagram of a kV radiation therapy system in accordance with one implementation of the present disclosure.

FIG. 1A is a block diagram of a kV radiation therapy system 100 in accordance with one implementation of the present disclosure. In the illustrated implementation of FIG. 1A, the kV radiation therapy system 100 includes a kV X-ray source 110, a detector 140, and an imager/tracker 150. The kV X-ray source 110 delivers X-rays to a pre-determined target lesion and surrounding tissue 130. The imager/tracker 150 determines the precise location of the target lesion. The kV X-ray source 110 and the detector 140 are generally disposed on a gantry.

Figure 1B:
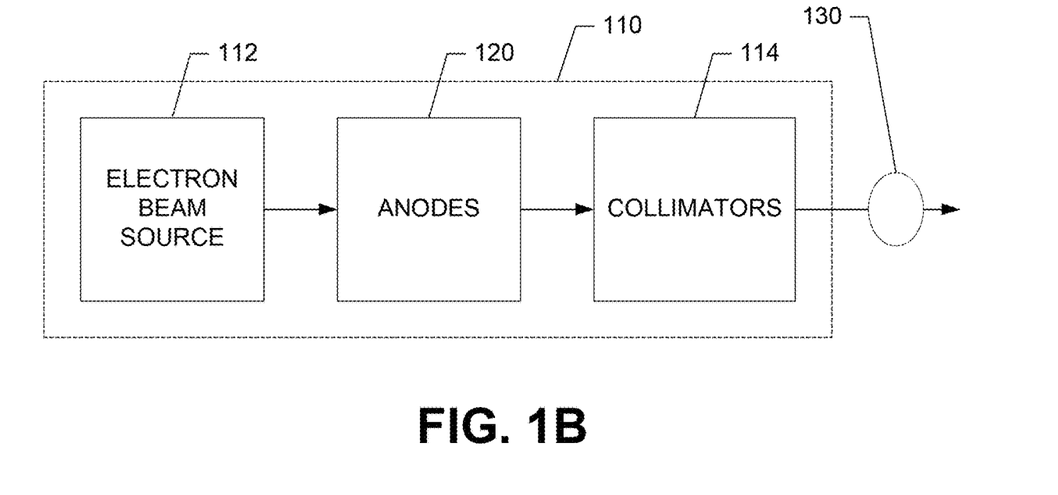
FIG. 1B is a detailed block diagram of the kV X-ray source in accordance with one implementation of the present disclosure.

FIG. 1B is a detailed block diagram of the kV X-ray source 110 in accordance with one implementation of the present disclosure. In the illustrated implementation of FIG. 1B, the kV X-ray source 110 includes an electron beam source (e.g., X-ray tube) 112, anodes 120, and collimators 114. In one implementation, the collimator is moveable to enable the collimator to adjust the convergence point.

Figure 1C:
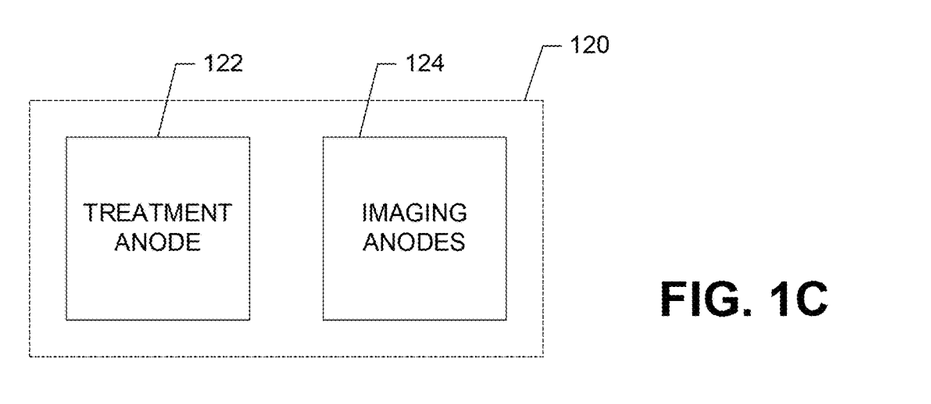
FIG. 1C is a detailed block diagram of the anodes which include a treatment anode (which generates a treatment beam) and imaging anodes (which enables real-time imaging and tracking)

FIG. 1C is a detailed block diagram of the anodes 120 which include a treatment anode 122 (which generates a treatment beam) and imaging anodes 124 (which enables planning imaging, real-time imaging and tracking).

In one implementation, the kV X-ray source 110 is intensity modulated with a 3-D trajectory using scanning electron beam and gantry rotation, which enables the treatment beam to enter the body over a much larger skin area and tissue volume. As stated above, the scanning electron beam is continuously swept over the treatment anode 122, which allows cooling with a chiller. In one implementation, the electron beam is "scanned" (or steered) using one or more steering magnets (housed around the beam exiting the electron beam source 112) to sweep over the anode 122. The steering magnet includes and can be one or more of dipole, quadrupole, and solenoid magnets.

When the electron beam strikes the anode 122, the anode generates X-rays near-isotropically such that the X-rays propagate in all directions. Thus, the collimator 114 is configured to direct the X-rays to the target lesion and surrounding tissue 130 by blocking X-rays not propagating towards the "convergence point" centered about the target lesion. The imaging anodes 124 are configured to provide planning imaging, real-time imaging and tracking of target lesion within the surrounding tissue 130 to enable precise targeting of the treatment beam to the target lesion within the surrounding tissue 130.

In one example implementation, the kV radiation therapy system 100 includes an electron beam source 112 (e.g., within the X-ray source 110) which rotates about a patient with cancerous lesion(s) positioned at the isocenter for up to a 30-minute treatment time. The electron beam source 112 delivers the treatment X-ray beam to a pre-determined target lesion (e.g., 1 cm sphere at the isocenter) by blocking all X-rays not propagating towards the convergence point (see FIGS. 5A and 5B for details). Thus, the X-ray tube (see FIG. 4 for details), with sufficient cooling and heat management, may accommodate 200 kVp, 200 mA (40 kW), 1-cm diameter electron beams that continuously scans across the 75×3 cm$^2$ tungsten anode continuously for up to 30 minutes. The scanning electron beam over a large anode area allows sufficient cooling to less than 400° C., which is the X-ray tube/source bake-out temperature that ensures operation without damage or outgassing. The 1-cm diameter electron beam focal spot size is one example of the above-mentioned "defocused electron beam" which maximizes flux and distributes the heat over a relatively large area. However, the spot size may vary according to the size and distance from the lesion.

Using the above example implementation (which includes appropriate phantoms containing a radiochromic film or Farmer type ionization chamber), the 3-D dose distributions for a lung cancer, for example, can be delivered in less than 30 minutes to validate the dose delivery within 5% of the predicted values. This dose distribution can be directly compared to those of the state-of-the-art standard linac MV treatment systems. In the event of complicated lesion shapes or larger volumes, both the source and the patient table can be moved during the treatment thereby distributing adequate dosing over the entire geometry.

For deep lesions, the higher tissue attenuation of the conventional kV X-ray therapy overdoses the skin and tissue upstream from the target lesion. Thus, it is highly desirable to have entry points of the treatment X-rays be distributed over as large an area as possible. An intensity-modulated kV X-ray source with 3-D trajectory (using a scanning electron beam and a gantry rotation) enables the entry points of the treatment X-rays to be distributed over a large area.

In one implementation of the intensity-modulated kV X-ray source with 3-D trajectory, the X-ray tube is mounted on a gantry that rotates the tube while the electron beam is magnetically steered (using steering coils of the magnets) onto the treatment anode (e.g., tungsten anode) orthogonal to the circular trajectory of the gantry. Thus, the locus of source positions becomes the surface of a cylinder (for 360° treatment plan). This geometry distributes the entry points of the treatment X-rays over a large skin area, thereby increasing the target lesion to skin dose. Therefore, the intensity of the X-ray can be "modulated" by varying the electron beam current (defined as amp or coulombs per second where 1 coulomb=$6.25 \times 10^{18}$ electrons) or varying the speed at which the electron beam is swept over the treatment anode. This is in contrast to the MV systems in which the modulation is performed by varying the pulse repetition frequency of pulses that are on the order of 5 microseconds.

Using the readily available CT scanner dose rate data for diagnostic exams, the dose delivered by the kV radiation therapy system can be estimated by assuming the quadratic dependence on kVp and linear dependence on current-time product (mAs). The abdominal CT with a 120 kV, 240 mA source delivers about 15 mGy for adults 25 years of age and older. Assuming that it takes about one second for the examination (which is normally the case), the kV radiation therapy system would deliver 35 mGy (=15×200/240×(200/120)2) every second. This corresponds to 2 Gy/min (=35× 60), which is within the neighborhood of 1-6 Gy/min delivered by typical MV systems. At 10 cm depth, the dose rates would be reduced by factors of about 0.2 and 0.5, for kV and MV systems, respectively. Therefore, the dose rate of the 200 kVp, 200 mA kV radiation therapy can be one to several Gy/min and should be competitive to a therapy based on MV systems. In fact, the kV radiation therapy system of the present disclosure may even be superior to the MV systems, because the kV X-rays can be collimated with rapid dose fall-off, whereas MV multi-leaf collimator systems produce dose distribution with poor dose fall-off due to thick and blunt edges of (usually) tungsten leaves. That is, the higher energy MV X-rays are harder to block because the blocking material needs to be thick (usually tungsten of about 1 cm or thicker), while the lower energy kV X-rays are easier to block usually with a thin lead sheets.

Figure 2:
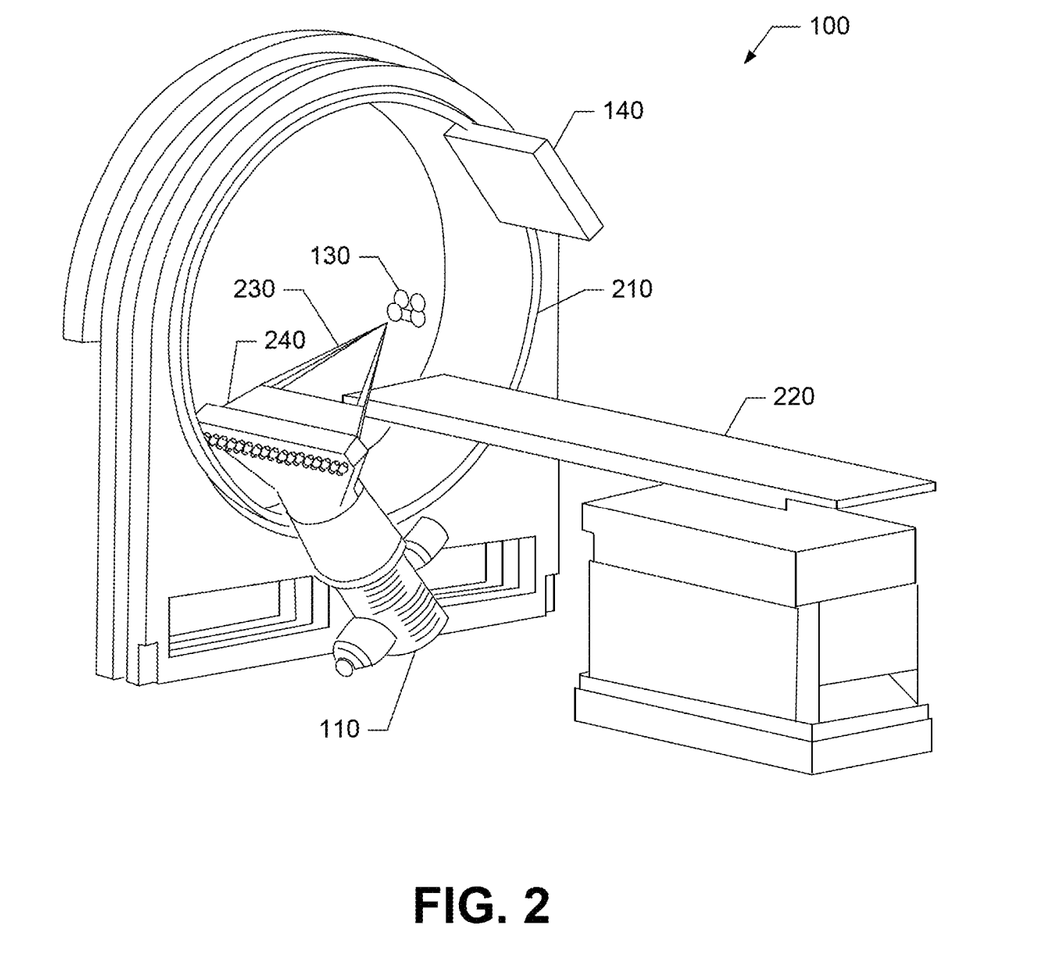
FIG. 2 is a perspective view of the kV radiation therapy system in accordance with one implementation of the present disclosure.

FIG. 2 is a perspective view of the kV radiation therapy system 100 in accordance with one implementation of the present disclosure. In the illustrated implementation of FIG. 2, the kV radiation therapy system 100 includes the kV X-ray source 110 and the detector 140. As stated above, the kV X-ray source 110 delivers the X-rays to the target lesion and surrounding tissue 130. In one implementation, the kV X-ray source 110 and the detector 140 are disposed on a gantry 210. Further, the gantry 210 may be configured to rotate about a patient lying on a flat surface 220 to enable the X-ray source 110 to illuminate the target lesion from various angles.

Figure 3:
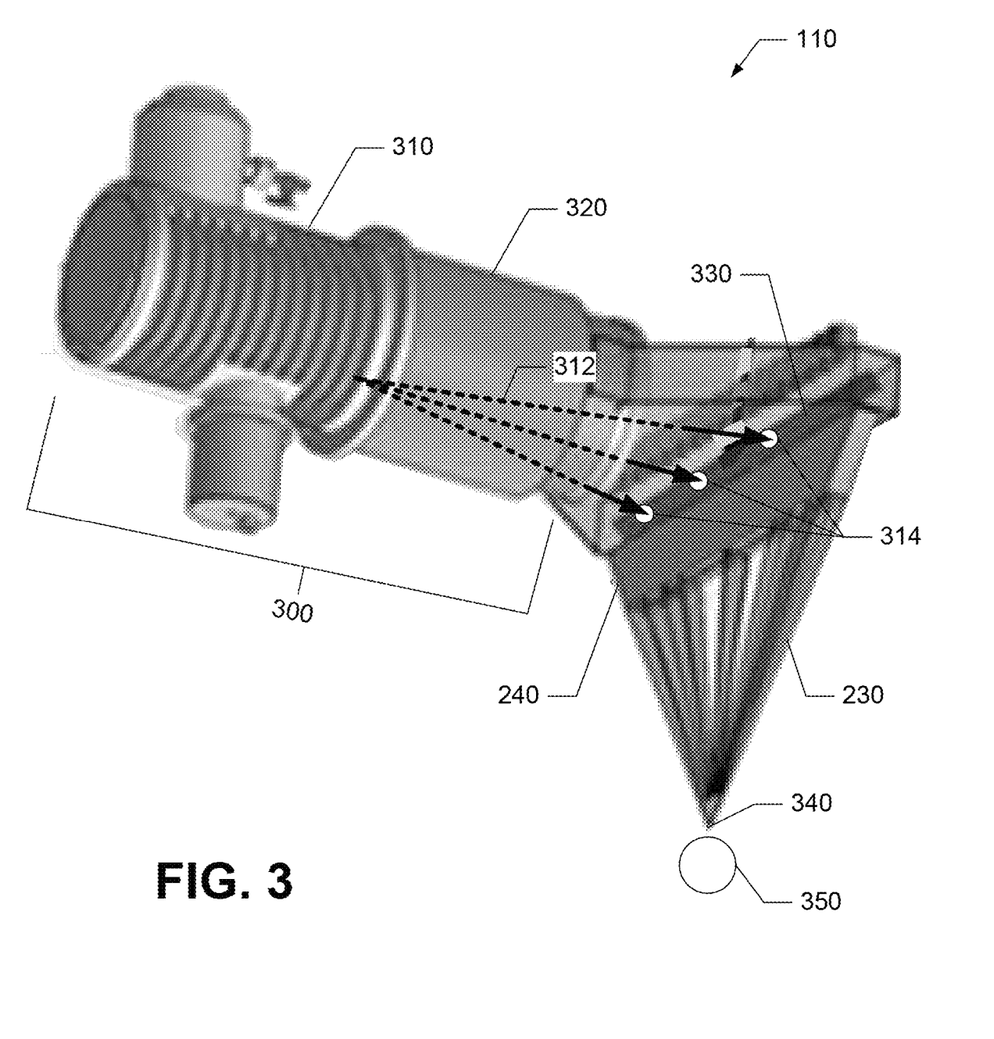
FIG. 3 is a detailed perspective view of the X-ray source including an X-ray tube in accordance with one implementation of the present disclosure.

FIG. 3 is a detailed perspective view of the X-ray source 110 including an X-ray tube 300 in accordance with one implementation of the present disclosure. In one implementation, the X-ray source 110 is configured to deliver the X-rays 230 (generated via a scanning electron beam 312) to a pre-determined target lesion 350 (e.g., 1 cm sphere at the isocenter) by blocking all X-rays not propagating towards a convergence point 340 (using an anode 330 and the collimator 240). In one implementation, the X-ray tube 300 includes an electron gun 310 and steering coils 320 configured with one or more magnets.

Figure 4:
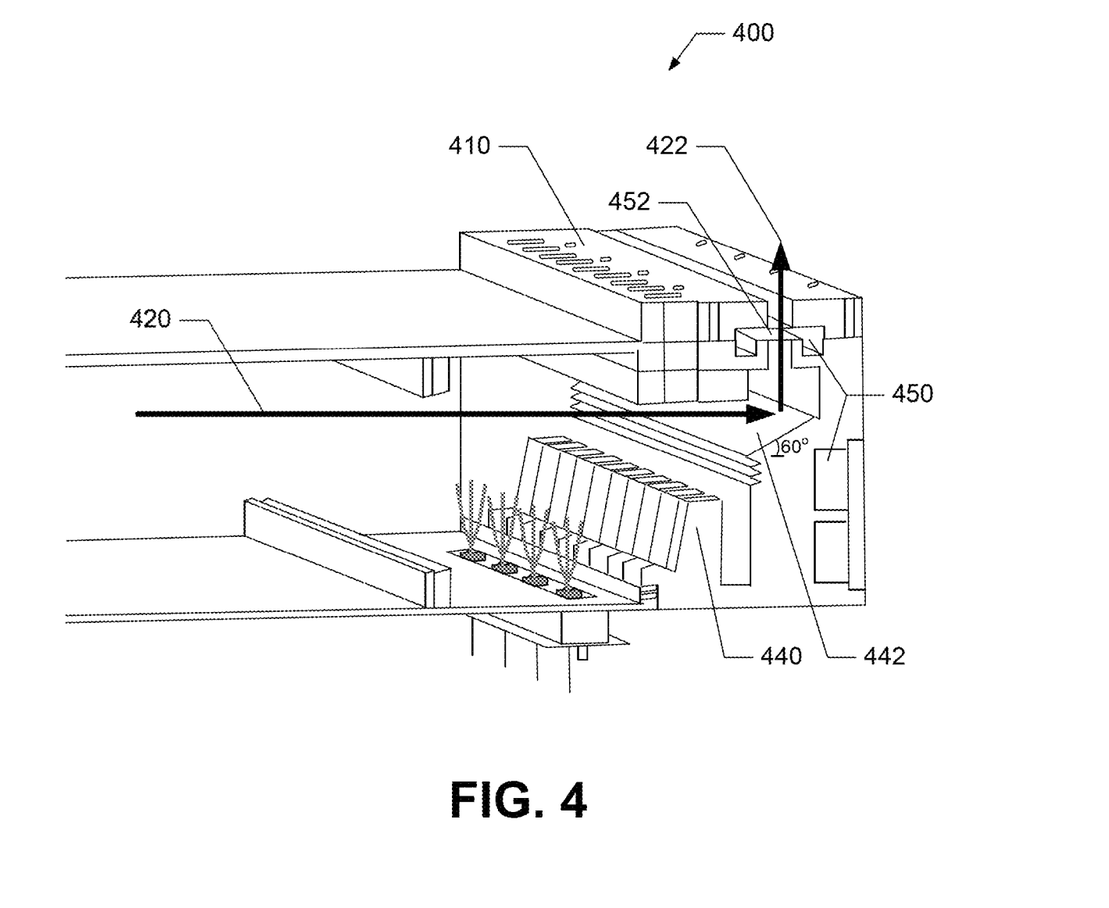
FIG. 4 is a cut-out perspective view of the X-ray tube in accordance with one implementation of the present disclosure.

In the illustrated implementation of FIG. 3, the electron gun 310 of the X-ray tube 300 generates and directs electron beams 312 toward the treatment anode 330. Since dwelling the electron beams 312 on the tungsten anode 330 can easily destroy the anode, the tungsten anode 330 is kept cool (e.g., water-cooled as shown in FIG. 4). The electron beams 312 are kept moving ("scanned" and/or "steered") at all time using the one or more magnets (i.e., steering coils 320) so that each beam falls on different part of the tungsten anode 330. Therefore, an intensity-modulated kV X-ray source 110 achieves a 3-D trajectory by adapting the magnetically-steered continuously scanning electron beams 312 (which are swept magnetically along the long axis of the anode 330) with the rotation therapy (which moves the resultant photons substantially perpendicular to the long axis by the mechanical motion of the gantry 210 shown in FIG. 2. The result is an inverted pyramid shape of photons with the apex 340 on the target lesion 350. Further, in one implementation, the electron gun 310 includes a defocusing unit which defocuses each electron beam to increase the size of the focal spot 314 and thus keep the anode 330 from melting. In one implementation, the above-described use of the scanning electron beam and gantry rotation enables the treatment beam 230 to enter the body over a much larger skin area and tissue volume.

As stated above, when the electron beams 312 strike the anode 330, the anode 330 generates X-rays isotropically to propagate in all directions. Thus, the collimator 240 is configured to direct the X-rays 230 to the target lesion 350 by blocking X-rays not propagating towards the "convergence point" 340 centered about the target lesion 350.

FIG. 4 is a cut-out perspective view of the X-ray source 400 near the treatment anode 442 (without the trapezoid shaped collimator shown in FIG. 3) in accordance with one implementation of the present disclosure. In the illustrated implementation of FIG. 4, as an electron beam 420 (e.g., beam size=1×1 $cm^2$) strikes a water-cooled tungsten treatment anode 442 (e.g., size=75×3 $cm^2$) with a tilt (e.g., 60°), X-rays 422 exit the source 400 through a water-cooled window 452. The large electron beam spot (e.g., size=1×2 $cm^2$) on the treatment anode 442 lessens the anode cooling requirements. In one implementation, cooling the 40 kW (=200 kV×200 mA) X-ray source for continuous operation is sufficient with 4 Gal/min of water pumped from an external 40 kW chiller through cooling water channels 450. In the illustrated implementation of FIG. 4, the collimator (shown in FIGS. 5A and 5B) (e.g., size=75×2×6 cm$^3$) directs the X-rays 422 to the target lesion by blocking all X-rays not directed towards the "convergence point" (e.g., point 340 in FIG. 3) centered about the target. The X-ray source 400 further includes imaging anodes 440. In another implementation, the collimator directs the X-rays 422 to the target lesion by blocking all X-rays not directed towards the "convergence region". The convergence region is a small volume in 3-D space, e.g., a sphere of one to few centimeters.

Figure 5A:
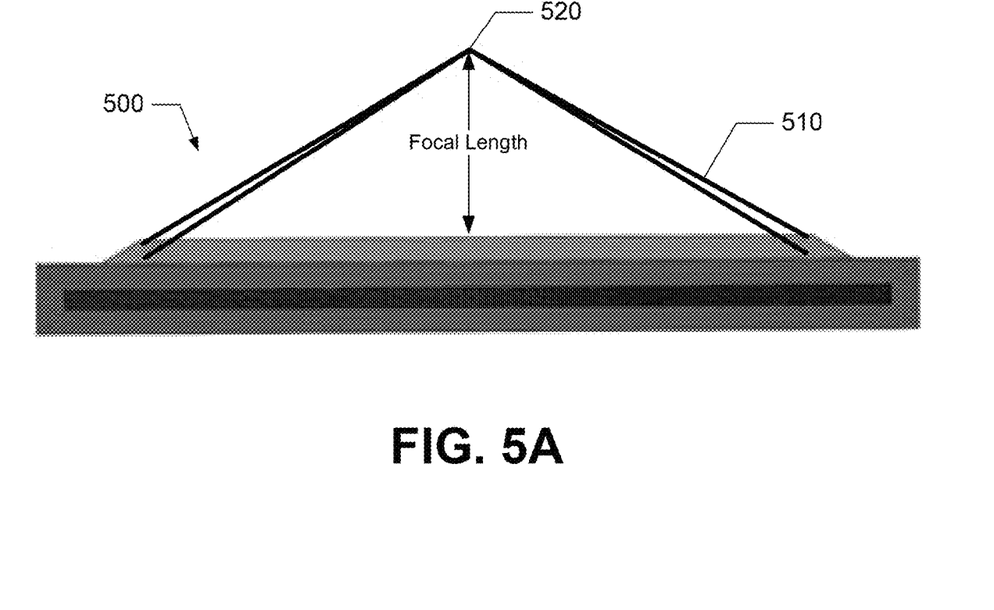
FIG. 5A shows the collimator configured to direct the X-rays toward a convergence point.
Figure 5B:
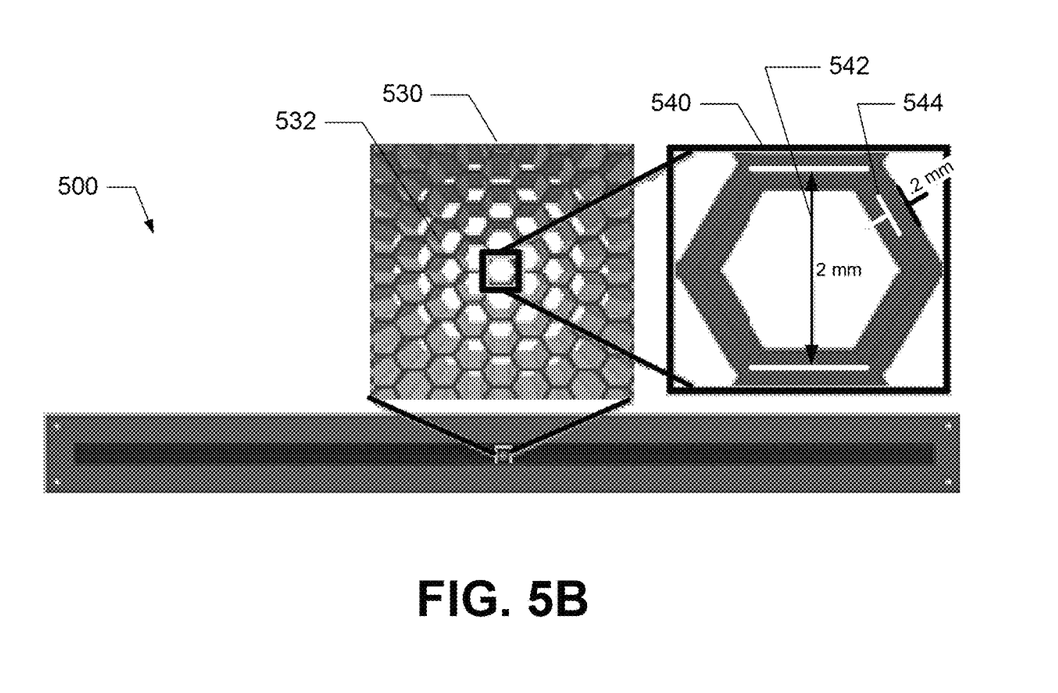
FIG. 5B shows a frontal view of the collimator with two zoomed views on top.

FIGS. 5A and 5B are diagrams showing a collimator 500 in accordance with one implementation of the present disclosure. FIG. 5A shows the collimator 500 configured to direct the X-rays 510 toward a convergence point 520. FIG. 5B shows a frontal view of the collimator 500 with two zoomed views 530, 540 on top.

In the illustrated implementation of FIG. 5B, the collimator 500 is constructed with hexagonal holes 532 (and associated septa) shown in the zoomed view 530. The hexagonal holes are configured to direct the X-rays to converge to a point at the convergence point 520. That is, in one implementation of the present disclosure, the cross sections of hexagonal holes 532 and the associated septa get smaller and thinner as the X-rays 510 are directed downstream towards the convergence point 520. In another implementation, the cross sections are rectangular.

The collimator design of FIG. 5B can be visually verified upon viewing the first zoomed view 530 taken with a virtual light source at the convergence point. It should be noted that the light source is mostly visible in the middle indicating a clear line of sight to the convergence point 520. Other views towards the convergence point from elsewhere at the entrance of the collimator will show similar renderings.

In one particular implementation shown in FIGS. 5A and 5B, the collimator 500 is configured as an array of hexagonal holes with a diameter D=2 mm 542 (at the entrance), a septa thickness t=0.2 mm 544 (at the entrance), and convergence point 520 at 40 cm from the exit of the collimator 500. The distance to the convergence point 520 (i.e., the focal length) dictates the rate at which the diameter and the septum thickness changes in size.

For the treatment, several collimators with different convergence points and with different treatment volumes can be used. Thus, collimator(s) can be chosen depending on a particular treatment plan. Several attachable collimators can be constructed for different target lesion sizes (e.g., sizes s=1, 2, 3, 4 cm) and focal lengths (e.g., focal lengths f=26, 36, 46 cm).

Referring back to FIG. 4, the real-time imaging and tracking capability of the kV radiation therapy system is enabled by the imaging anodes 440 (e.g., 19 imaging anodes can be used). During the treatment, the electron beam 420 may cycle through all imaging anodes 440 periodically. In one implementation, the electron beam 420 is focused onto one of the imaging anodes 440 for 1-10 msec (and similarly cycles through all imaging anodes) and a projection image is captured by the detector (e.g., a flat panel detector 140 of FIG. 2). The projection images (e.g., projection images captured by the detector 140) are then used to reconstruct a 3-D volumetric image (using, for example, a tomosynthesis algorithm to detect and display the image of the target lesion). An accurate location of the target lesion allows accurate positioning for the accurate and precise dose delivery. The use of the tomosynthesis algorithm enables accurate 3-D reconstruction of the target lesion (to render enough details of the cancerous lesions (e.g., in the lung, which moves during treatment) to allow detection and tracking) using 19 projection images.

Figure 6A:
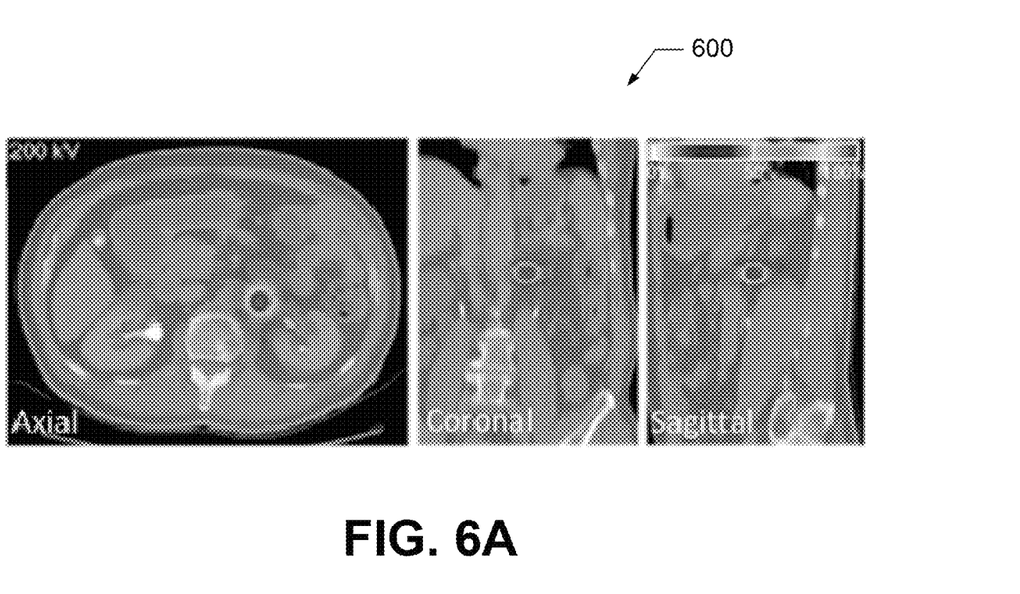
FIG. 6A shows Monte Carlo-modeled patient dose distributions using the 200 kVp, 200 mA kV arc therapy (KVAT)
Figure 6B:
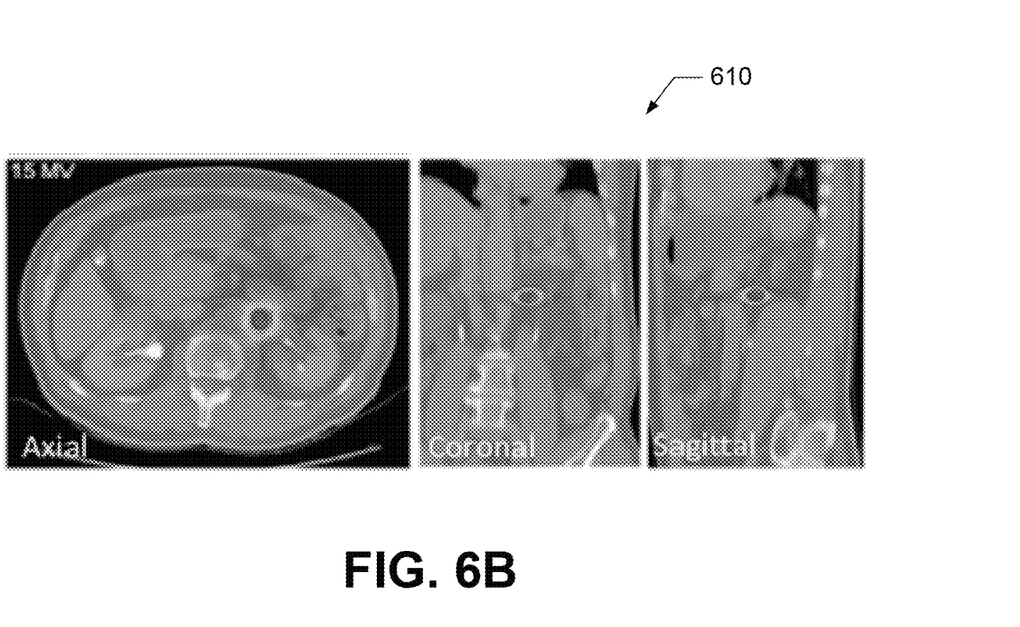
FIG. 6B shows Monte Carlo-modeled patient dose distributions using 15 megavoltage (MV) linear accelerator (linac) volumetric modulated arc therapy (VMAT)

FIG. 6A shows Monte Carlo-modeled patient dose distributions 600 using the 200 kVp, 200 mA kV arc therapy (KVAT). FIG. 6B shows Monte Carlo-modeled patient dose distributions 610 using 15 MV linac volumetric modulated arc therapy (VMAT).

FIGS. 6A and 6B show both KVAT and VMAT exhibiting similarly excellent dose profiles for treatment of deep-seated lesions. Thus, a therapy system using KVAT can be competitive to a VMAT system, if the cooling of anodes can be solved.

Figure 7A:
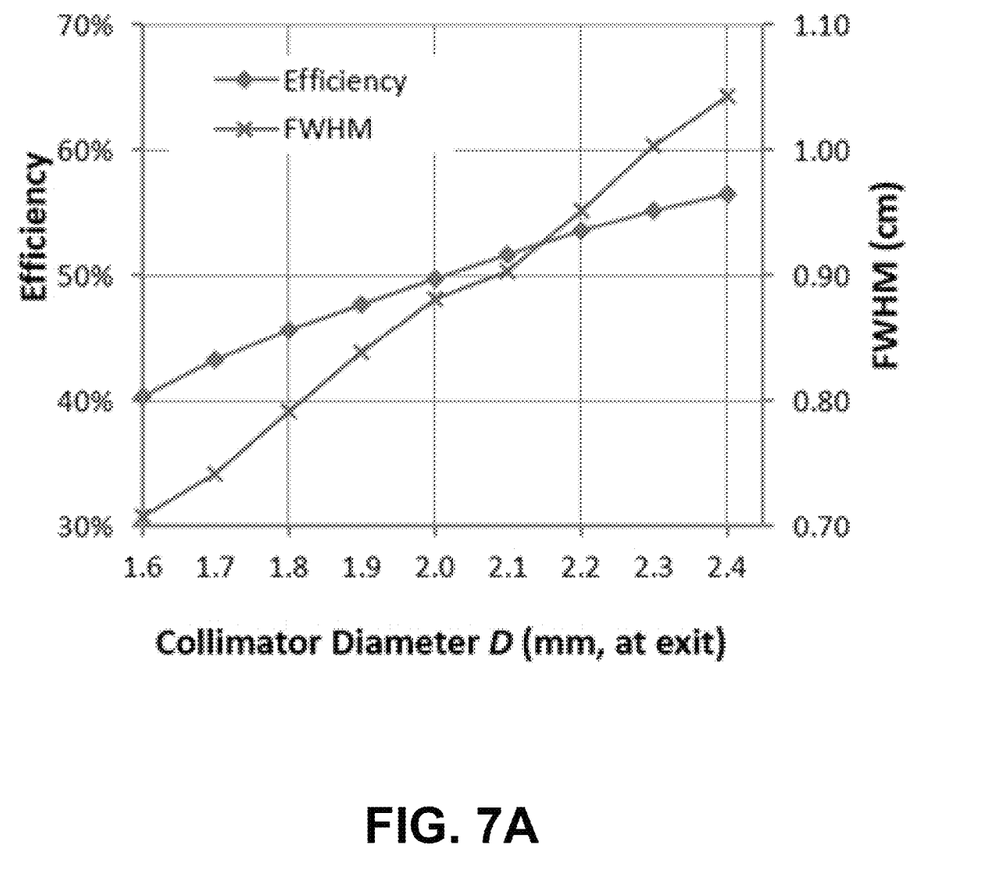
FIG. 7A shows the collimator efficiency and the full-width-half-maximum (FWHM) as functions of a collimator hole size (D) at a fixed septum thickness (t=0.2 mm) at the collimator exit.
Figure 7B:
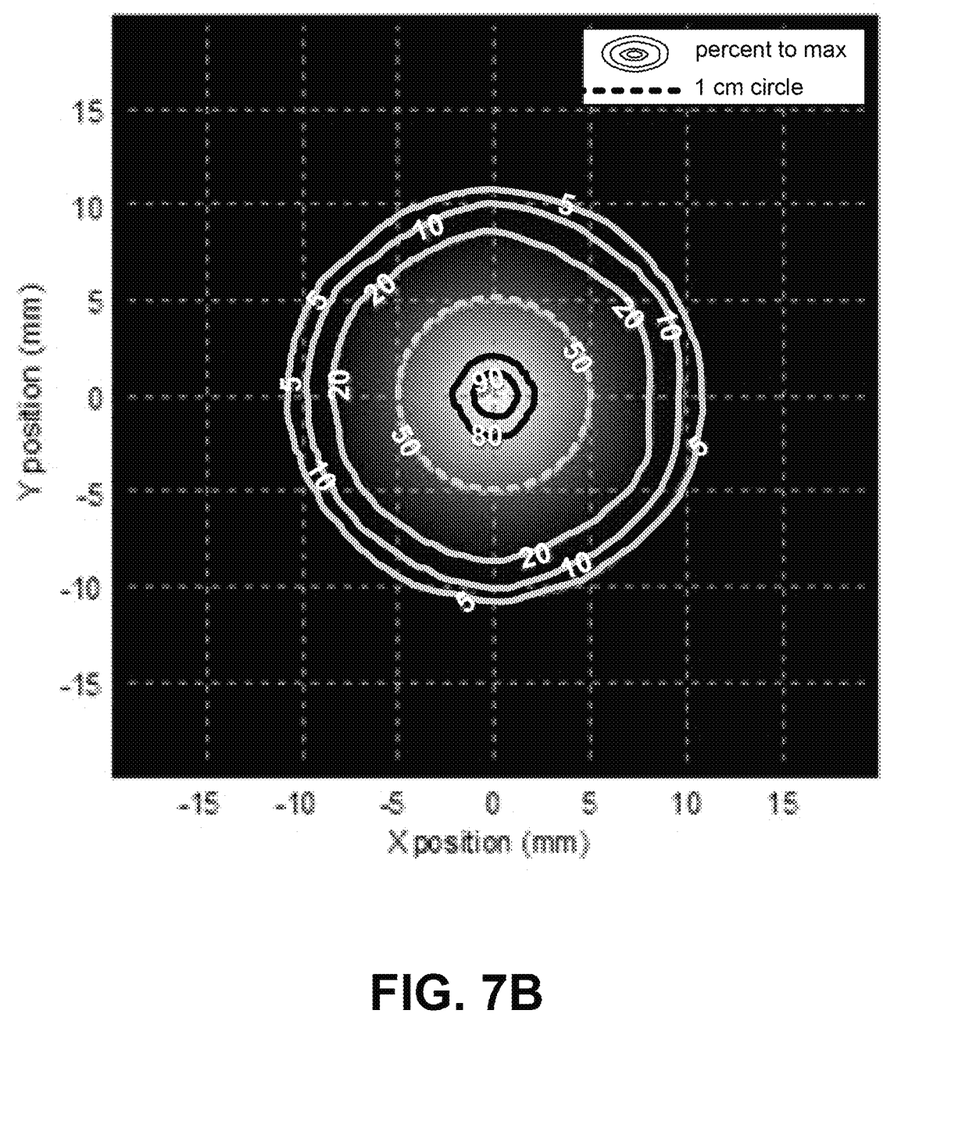
FIG. 7B shows the dose distribution for (D, t)=(2.3 mm, 0.2 mm) using an X-ray source of size 75×2 $cm^2$ on the plane of the anode with an appropriate tilt (30° from the plane of the electron beam path)

FIGS. 7A and 7B are graphs showing the performance of a collimator (e.g., collimator 500) used in the kV radiation therapy system.

FIG. 7A shows the collimator efficiency and the full-width-half-maximum (FWHM) as functions of a collimator hole size (D) at a fixed septum thickness (t=0.2 mm) at the collimator exit. FIG. 7A offers an important design guideline in selecting the septum thickness (t) and the collimator hole size (D). For instance, at FWHM of 1.0 cm, the efficiency of 55% can be achieved.

FIG. 7B shows the actual delivered dose profile at a particular setting of D and t. FIG. 7B shows the dose distribution for (D, t)=(2.3 mm, 0.2 mm) using an X-ray source of size 75×2 cm$^2$ on the plane of the anode with an appropriate tilt (30° from the plane of the electron beam path). The detector-centric ray-casting was used with the detection plane located 40 cm from the exit face of the collimator.

The results shown in FIGS. 7A and 7B indicate that the shape of the dose distribution does not depend much on the septum thickness (t), but it does depend on the collimator hole size (D).

Figure 8:
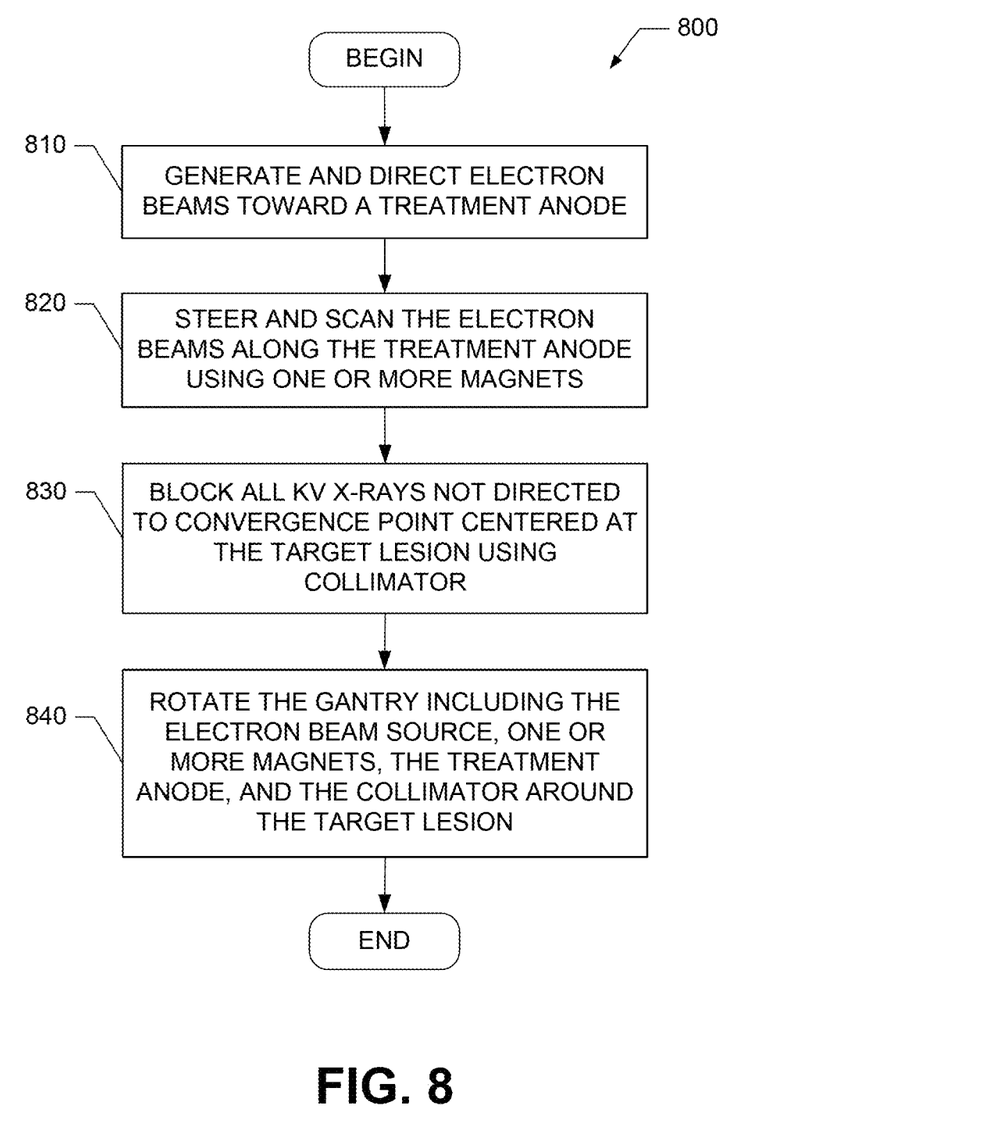
FIG. 8 is a flow diagram illustrating a process 800 for delivering kV X-rays toward a target lesion within a body in accordance with one implementation of the present disclosure.

FIG. 8 is a flow diagram illustrating a process 800 for delivering kV X-rays toward a target lesion within a body in accordance with one implementation of the present disclosure. At block 810, electron beams are generated and directed toward a treatment anode. The electron beams are then steered and scanned along the treatment anode, at block 820, using one or more magnets so that the treatment anode generates the kV X-rays. At block 830, all of the kV X-rays not directed to a convergence point centered at the target lesion are blocked out using a collimator. The electron beam source, the one or more magnets, the treatment anode, and the collimator are then rotated around the target lesion, at block 840.

In one implementation, the process 800 further includes adjusting a speed at which the electron beams are steered and scanned to modulate a dose rate of the kV X-rays to the target lesion. In another implementation, the steering and scanning includes constantly moving the electron beams along a longitudinal axis of the treatment anode. In yet another implementation, the process 800 further includes modulating an intensity of the kV X-rays. In yet another implementation, the modulating includes varying an electron beam current. In yet another implementation, the modulating includes varying a speed at which the electron beams are steered and scanned along the treatment anode. In yet another implementation, the process 800 further includes defocusing the electron beams directed toward the treatment anode so that spot sizes of the electron beams are increased. In yet another implementation, the blocking out of the X-rays further includes outputting the kV X-rays from the collimator in a plane substantially perpendicular to the electron beams steered and scanned onto the treatment anode. In yet another implementation, the collimator is moveable, and the process further includes real-time imaging the target lesion using a plurality of imaging anodes to enable the moveable collimator to adjust so that the convergence point follows the target lesion that moves (e.g., with breathing). In a further implementation, the process 800 further includes cooling the treatment anode using a water-cooling unit.

Various modifications to these implementations will be readily apparent to those skilled in the art, and the generic principles described herein can be applied to other implementations without departing from the spirit or scope of the disclosure. Accordingly, the techniques are not limited to the specific examples described above. Thus, it is to be understood that the description and drawings presented herein represent a presently possible implementation of the disclosure and are therefore representative of the subject matter that is broadly contemplated by the present disclosure. It is further understood that the scope of the present disclosure fully encompasses other implementations that may become obvious to those skilled in the art and that the scope of the present disclosure is accordingly limited by nothing other than the appended claims.

The invention claimed is:

1. An apparatus comprising:
   a treatment anode;
   an electron beam source to generate an electron beam toward the treatment anode;
   at least one magnet to steer and scan the electron beam along the treatment anode; and
   a collimator comprising holes having cross-sections and associated septa, wherein the cross-sections are smaller and the associated septa are thinner toward a convergence point, the collimator to block X-rays not propagating towards the convergence point.

2. The apparatus of claim 1, the treatment anode generating X-rays in response to the at least one magnet scanning the electron beam along the treatment anode, wherein the collimator blocks the generated kV X-rays not directed to the convergence point.

3. The apparatus of claim 2, further comprising
   a gantry configured to mount and rotate about an axis the electron beam source, the at least one magnet, the treatment anode, and the collimator.

4. The apparatus of claim 2, the at least one magnet including a dipole magnet, a quadrupole magnet, and a solenoid magnet.

5. The apparatus of claim 2, further comprising
   an imaging anode.

6. The apparatus of claim 1, further comprising
   a water-cooling unit coupled to the treatment anode, the water-cooling unit configured to cool the treatment anode.

7. The apparatus of claim 1, wherein the electron beam source includes a defocusing unit to defocus the electron beam directed toward the treatment anode.

8. The apparatus of claim 1, wherein the treatment anode comprises tungsten.

9. The apparatus of claim 1, wherein the at least one magnet includes at least one of dipole, quadrupole, and solenoid magnets.

10. A method for delivering kV X-rays toward a target lesion within a body, the method comprising:
    generating and directing an electron beam toward a treatment anode;
    steering and scanning the electron beam along the treatment anode using at least one magnet to generate the kV X-rays; and
    blocking with a collimator the kV X-rays not directed to a convergence point centered at the target lesion, the collimator comprising holes having cross-sections and associated septa, wherein the cross-sections are smaller and the associated septa are thinner toward a convergence point.

11. The method of claim 10, further comprising
    adjusting a speed at which the electron beam is steered and scanned to modulate a dose rate of the kV X-rays to the target lesion.

12. The method of claim 10, wherein the steering and scanning comprises moving the electron beam along a longitudinal axis of the treatment anode.

13. The method of claim 10, further comprising modulating an intensity of the kV X-rays.

14. The method of claim 13, wherein the modulating comprises varying an electron beam current.

15. The method of claim 13, wherein the modulating comprises varying a speed at which the electron beam is steered and scanned along the treatment anode.

16. The method of claim 10, further comprising defocusing the electron beam directed toward the treatment anode.

17. The method of claim 10, further comprising rotating about the target lesion the treatment anode, the collimator, and a source of the electron beam.

18. The method of claim 10, further comprising moving the collimator in three dimensions with respect to the target lesion.

19. The method of claim 18, further comprising
    real-time imaging the target lesion using an imaging anode to enable tracking of the target lesion and adjustment of the collimator to move the convergence point to the target lesion.

20. The method of claim 10, further comprising cooling the treatment anode using a water-cooling unit.

* * * * *